United States Patent
Yamada et al.

(10) Patent No.: US 11,578,435 B2
(45) Date of Patent: Feb. 14, 2023

(54) WOVEN FABRIC AND METHOD FOR MANUFACTURING SAME

(71) Applicant: Toray Industries, Inc., Tokyo (JP)

(72) Inventors: Satoshi Yamada, Otsu (JP); Nobuaki Tanaka, Otsu (JP); Hiroshi Tsuchikura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 250 days.

(21) Appl. No.: 16/769,606

(22) PCT Filed: Nov. 8, 2018

(86) PCT No.: PCT/JP2018/041497
§ 371 (c)(1),
(2) Date: Jun. 4, 2020

(87) PCT Pub. No.: WO2019/116792
PCT Pub. Date: Jun. 20, 2019

(65) Prior Publication Data
US 2020/0318261 A1    Oct. 8, 2020

(30) Foreign Application Priority Data

Dec. 15, 2017    (JP) .............................. JP2017-240553

(51) Int. Cl.
*D03D 11/00*    (2006.01)
*D03D 17/00*    (2006.01)
(Continued)

(52) U.S. Cl.
CPC .............. *D03D 17/00* (2013.01); *A61F 2/06* (2013.01); *A61L 27/50* (2013.01); *D03D 1/00* (2013.01);
(Continued)

(58) Field of Classification Search
CPC ............ D03D 17/00; D03D 1/00; D03D 3/02; D03D 3/08; D03D 15/68; A61F 2/06;
(Continued)

(56) References Cited

U.S. PATENT DOCUMENTS 2,424,771 A    7/1947   Preneta
3,096,560 A *  7/1963   Liebig ...................... A61F 2/06
                                                          28/165
(Continued)

FOREIGN PATENT DOCUMENTS

CN    103643385 A    3/2014
EP       1495172 B1   5/2007
(Continued)

OTHER PUBLICATIONS

Chinese Office Action for Chinese Application No. 201880079847.X, dated Jan. 26, 2021, 8 pages.
(Continued)

*Primary Examiner* — Robert H Muromoto, Jr.
(74) *Attorney, Agent, or Firm* — RatnerPrestia

(57) ABSTRACT

It is an object to provide a woven fabric which can stably form a folding shape superior in shape retention and followability and which can be sewn while maintaining the folding structure, and also to provide a method for manufacturing the same. There is provided a woven fabric having pleats, wherein the height of the pleats is 2 to 10 times the average diameter of yarns arranged in the same direction as the pleats.

9 Claims, 1 Drawing Sheet

(51) Int. Cl.
*A61F 2/06* (2013.01)
*A61L 27/50* (2006.01)
*D03D 1/00* (2006.01)
*D03D 3/02* (2006.01)
*D03D 3/08* (2006.01)
*D06C 7/02* (2006.01)
*D06J 1/00* (2006.01)
*D03D 15/68* (2021.01)
*A61F 2/04* (2013.01)

(52) U.S. Cl.
CPC .............. *D03D 3/02* (2013.01); *D03D 3/08* (2013.01); *D03D 15/68* (2021.01); *D06C 7/02* (2013.01); *D06J 1/00* (2013.01); *A61F 2240/001* (2013.01)

(58) Field of Classification Search
CPC .... A61F 2240/001; A61L 27/50; A61L 27/18; D06C 7/02; D06J 1/00; D10B 2509/06; D06M 11/00
See application file for complete search history.

(56) References Cited

U.S. PATENT DOCUMENTS

| | | | |
|---|---|---|---|
| 3,822,727 A | 7/1974 | Small et al. | |
| 4,044,404 A * | 8/1977 | Martin | D04H 1/728 623/1.42 |
| 4,652,263 A * | 3/1987 | Herweck | A61F 2/06 623/1.33 |
| 5,282,846 A | 2/1994 | Schmitt | |
| 5,697,978 A * | 12/1997 | Sgro | A61F 2/0063 606/151 |
| 5,749,919 A * | 5/1998 | Blanc | A61F 2/88 606/198 |
| 5,873,906 A * | 2/1999 | Lau | A61F 2/92 606/198 |
| 6,019,791 A * | 2/2000 | Wood | A61F 2/2445 623/2.11 |
| 6,746,458 B1 * | 6/2004 | Cloud | A61B 17/04 602/41 |
| 10,070,949 B2 * | 9/2018 | Tsuchikura | A61L 27/507 |
| 11,051,833 B2 * | 7/2021 | Martin | A61B 17/221 |
| 2002/0173804 A1 * | 11/2002 | Rousseau | A61B 17/00234 606/151 |
| 2004/0037813 A1 * | 2/2004 | Simpson | A61L 15/32 424/443 |
| 2005/0070994 A1 | 3/2005 | Sievers et al. | |
| 2010/0168872 A1 * | 7/2010 | Brown | A61L 27/3804 623/23.72 |
| 2011/0011407 A1 * | 1/2011 | Townsend | A61F 2/0045 128/834 |
| 2012/0330347 A1 * | 12/2012 | Becking | A61B 17/12172 606/200 |
| 2013/0289713 A1 * | 10/2013 | Pearson | A61F 2/954 623/1.35 |
| 2015/0313593 A1 * | 11/2015 | Patenaude | A61B 17/0466 128/207.14 |
| 2016/0339265 A1 * | 11/2016 | Asao | A61N 5/10 |
| 2018/0236123 A1 * | 8/2018 | Manoryk | A61L 26/0066 |
| 2020/0318261 A1 * | 10/2020 | Yamada | A61F 2/06 |
| 2020/0337823 A1 * | 10/2020 | Bailly | A61B 17/0057 |
| 2021/0007838 A1 * | 1/2021 | Tanaka | A61F 2/06 |

FOREIGN PATENT DOCUMENTS

| | | |
|---|---|---|
| JP | 4310757 | 5/1968 |
| JP | 62243847 A | 10/1987 |
| JP | 04226647 A | 8/1992 |
| JP | 2001161726 A | 6/2001 |
| JP | 2005511241 A | 4/2005 |
| JP | 2011153394 A | 8/2011 |
| WO | 03087449 A1 | 10/2003 |

OTHER PUBLICATIONS

Chinese Office Action for Chinese Application No. 201880079847.X, dated Aug. 13, 2021 with translation, 17 pages.
Extended European Search Report for European Application No. 18887406.9, dated May 14, 2021, 8 pages.
International Search Report and Written Opinion for International Application No. PCT/JP2018/041497, dated Jan. 22, 2019, 6 pages.

* cited by examiner

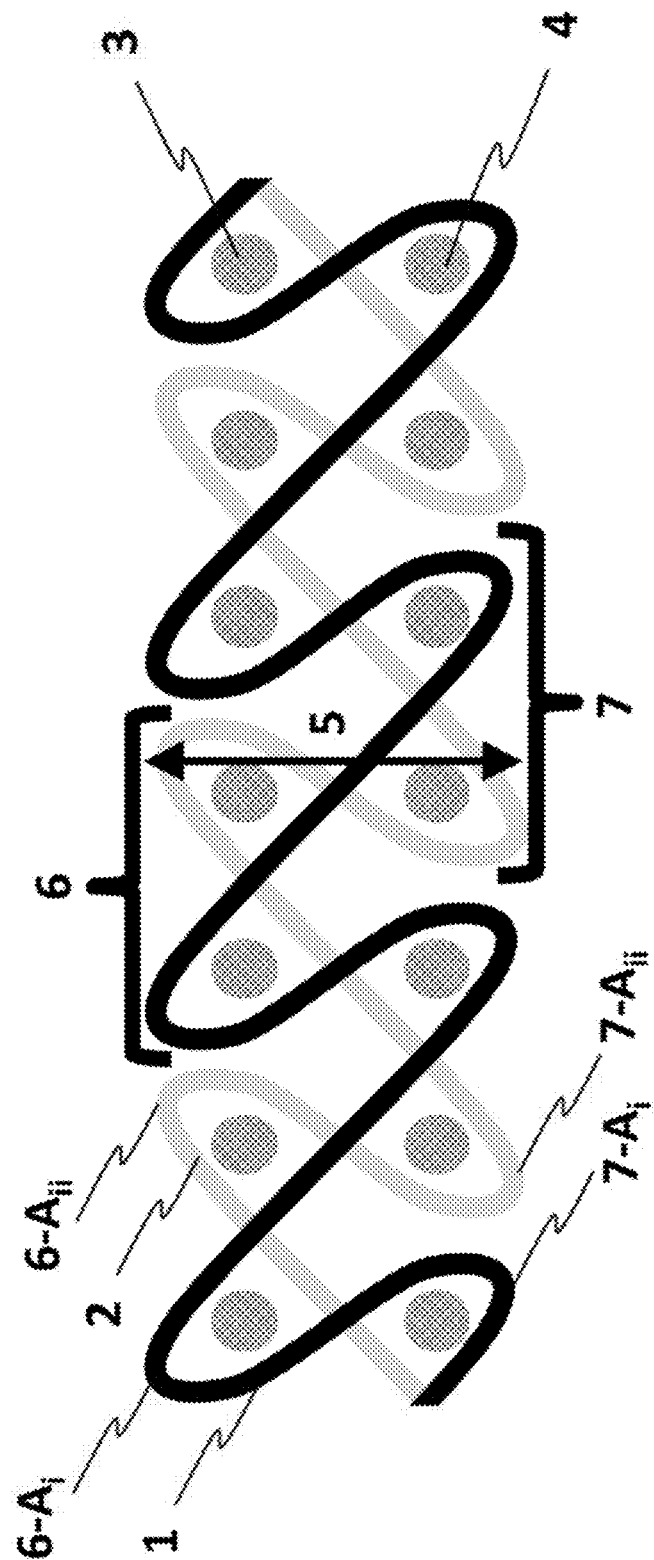

WOVEN FABRIC AND METHOD FOR MANUFACTURING SAME

CROSS REFERENCE TO RELATED APPLICATIONS

This is the U.S. National Phase application of PCT/JP2018/041497 filed Nov. 8, 2018 which claims priority to Japanese Patent Application No. 2017-240553, filed Dec. 15, 2017, the disclosures of each of these applications being incorporated herein by reference in their entireties for all purposes.

FIELD OF THE INVENTION

The present invention relates to a woven fabric and a method for manufacturing the same.

BACKGROUND OF THE INVENTION

Conventionally, various woven fabrics with a three-dimensional shape to be used for such applications as clothing have been proposed.

For example, Patent Document 1 discloses a fabric comprising a woven fabric constituted by intersecting warps and wefts each other, in which heat-shrinkable yarns are arranged at intervals of a prescribed number of wefts such that a folding shape is generated by the addition of heat. Specifically, there is disclosed a technology that a desired three-dimensional shape is formed by only applying heat treatment without performing press processing due to the configuration that the heat-shrinkable yarns are not worn as warps but are arranged to expose only on one side of the fabric at the site where the folding shape is to be formed. In addition, there is also disclosed a technology that if a heat-shrinkable yarn having water solubility is used, it is possible to realize a desired three-dimensional shape and concurrently remove aesthetic inconvenience by performing washing treatment after a frame attachment step.

Further, Patent Document 2 discloses a fancy woven fabric characterized in that a single-woven tissue part and a bag-shaped part composed of a plurality of layers formed using fiber yarns that constitute the single-woven tissue part are present alternately and intermittently, and one side of the bag-shaped part is bulged while being slack with respect to the other opposing side. This is a technology in which high heat retention can be achieved by a novel fiber structure in which air is contained in the bag-shaped part

PATENT DOCUMENTS

Patent Document 1: Japanese Patent Laid-open Publication No. 2011-153394
Patent Document 2: Japanese Patent Laid-open Publication No. 62-243847

SUMMARY OF THE INVENTION

However, since the woven fabric textile disclosed in Patent Document 1 forms a desired three-dimensional shape by only applying heat treatment without press processing, there is a problem that variations in heat treatment conditions greatly affect the formation of the three-dimensional shape, so that the folding shape cannot be formed stably.

Further, in the fancy woven fabric disclosed in Patent Document 2, one side of the bag-shaped part is bulged while being slack with respect to the other opposing side and the slack side of the bag-shaped part is fixed to the other side. Thus, the slack of the bag-shaped part cannot be used effectively and the bag-shaped part will bend if it is not used properly. If it is used at a site which moves such as a joint, it cannot follow the movement and forms wrinkles. Further, since the bag-shaped part is fixed to the other side, it is necessary to sew the woven fabric while maintaining the slack of the bag-shaped part, but it is difficult to perform sewing without bending the bag-shaped part. For this reason, there is a problem that it can be used limitedly for general and functional clothing that is required to have designability and followability to the body. Further, in medical applications, especially in such applications as tubularly woven artificial blood vessels, shunts, and stent grafts, the tube tends to bend due to the problematic followability and there is a problem in kink resistance.

It is an object of the present invention to improve such problems with the conventional technologies and provide a woven fabric that can stably form a folding shape with superior shape retention and followability and can be sewn while maintaining a folding structure. Further, a second challenge of the present invention is to provide a manufacturing method by which the aforementioned woven fabric can be manufactured well.

In order to solve such a problem, the present invention according to exemplary embodiments has any of the following configurations.

(1) A woven fabric having a pleat, the pleat having a height of 2 to 10 times an average diameter of a yarn arranged in the same direction as the pleat.

(2) The woven fabric according to the above (1), wherein 60% by mass or more of the yarn constituting the woven fabric is a thermoplastic fiber.

(3) The woven fabric according to the above (2), wherein the thermoplastic fiber is an inelastic fiber.

(4) The woven fabric according to the above (3), wherein the inelastic fiber is a polyester fiber.

(5) The woven fabric according to any one of the above (1) to (4), wherein part or all of the yarns constituting the woven fabric are multifilaments composed of filaments having a single yarn diameter of 6 μm or less.

(6) The woven fabric according to any one of the above (1) to (5), wherein the woven fabric is used for medical use.

(7) The woven fabric according to any one of the above (1) to (6), wherein the woven fabric is in a tubular form.

(8) An artificial blood vessel comprising the woven fabric in a tubular form according to the above (7) as a substrate.

(9) A method for manufacturing a woven fabric, including the following steps (a) to (d):

(a) a step of using a yarn to be removed as part of warps or wefts and weaving a fabric while folding a yarn arranged in parallel with the yarn to be removed, (b) a heat treatment step of setting a crimp of the folded yarn, (c) a step of removing the yarn to be removed after the step (b), (d) a heat treatment step of setting the crimp of the folded yarn after the step (c).

According to the present invention, it is possible to provide a woven fabric that can stably form a folding shape with superior shape retention and followability and can be sewn while maintaining a folding structure.

When such a woven fabric is made in tubular form, it can be beneficially used for industrial applications such as transport hoses for a fluid or a powder, protective hoses for linear bodies such as wires, cables and conduits, and tubular filters, as well as medical applications such as artificial blood vessels, shunt substrates, and stent grafts. In particular, it can be suitably used as artificial blood vessels.

Further, according to the manufacturing method of the present invention, the above-described woven fabric can be manufactured well.

BRIEF DESCRIPTION OF THE DRAWINGS

The FIGURE is a schematic diagram of a woven fabric showing one embodiment of the present invention, and is a diagram in which the woven fabric is cut in a direction intersecting with the pleating direction.

DETAILED DESCRIPTION OF EMBODIMENTS OF THE INVENTION

The woven fabric according to an embodiment of the present invention is characterized in that it has pleats and the pleat height is 2 to 10 times the average diameter of the yarns arranged in the same direction as the pleats. Preferably, it is in the range of 2 to 5 times. When the pleat height is twice or more, the woven fabric is superior in followability and shape retention and can form a pleated shape regularly and stably. If it is more than 10 times, the shape retention of a pleated shape is poor, so that it is difficult to obtain a pleated shape stably and sewability gets worse, too.

Herein, the term "pleat" refers to a state in which a mountain part and a valley part are formed alternately and repeatedly on both the front and back sides of a textile and the mountain parts of the front side of the textile are the valley parts on the back side of the textile. The "pleat height" refers to the height from a valley bottom part to a mountain top part of the "pleat" described above on the front or back side of the textile. In addition, the "average diameter of yarns" refers to a value calculated by observing a yarn bundle in a cross section in the perpendicular direction (thickness direction) of the woven fabric and calculating it from the distance between the top and the bottom in the vertical direction (thickness direction) of the woven fabric.

The yarns (warps and wefts) constituting the woven fabric of the present invention are preferably occupied 60% by mass or more by thermoplastic fibers, and more preferably 80% by mass or more by thermoplastic fibers. It is preferable to adjust the content of the yarns to be used for the woven fabric in the above range in terms of the dimensional stability of the woven fabric and the shape retention of a pleated shape and in terms of the pleated shape being likely to be formed more stably and regularly.

Examples of the thermoplastic fiber include nylon fiber, polyester fiber, etc., and it is more preferable to use a so-called inelastic fiber. Inelastic fibers tend to increase the strength and dimensional stability as a woven fabric. As used herein, the term "inelastic fiber" refers to a fiber made of fibers not having the so-called rubber-like elasticity, and is a type of fiber different from the so-called elastic fibers having rubber-like elasticity, which are made of a material superior in extensibility and resilience, such as a thermoplastic elastomer, including polyether elastomers, polysulfide elastomers, polyurethane elastomers, etc. In an embodiment of the present invention, even if an inelastic yarn is used, the woven fabric itself has stretchability.

As the thermoplastic fiber, a polyester fiber is particularly preferable in terms of strength and dimensional stability. Examples of the polyester fiber include fibers made of polyethylene terephthalate, polybutylene terephthalate, polypropylene terephthalate, a copolymer thereof, or the like.

Preferably, part or all of the yarns (warps and wefts) constituting the woven fabric of the present invention are multifilaments composed of filaments having a single yarn diameter of 6 μm or less. It is preferable to adjust the single yarn diameter into the above range because the flexibility is improved and because a pleated shape superior in followability is likely to be formed stably and regularly due to the resultant formation of a denser structure.

The yarns (warps and wefts) constituting the woven fabric of the present invention are not particularly limited, but twisted yarns, false twisted yarns, paralleled yarns, etc. can be appropriately used.

The weave density of yarns in the pleating direction is affected by the diameter of the yarns to be used, but it is preferable to achieve eventually (that is, after performing various steps) a weave density of 50 to 600 yarns/inch (2.54 cm), more preferably 80 to 500 yarns/inch (2.54 cm), and even more preferably 100 to 450 yarns/inch (2.54 cm). It is preferable to adjust the weave density into the above range because the structure of the woven fabric is thereby stabilized and a pleated shape superior in shape retention is likely to be formed stably and regularly.

The weave density of the yarns extending in the direction intersecting with the pleating direction is not particularly limited, and may be appropriately set according to the application in which the woven fabric is used.

The method for manufacturing the woven fabric according to the present invention is not particularly limited, but is, for example, as follows. First, using yarns to be removed such as soluble yarns as part of the warps or the wefts to constitute a woven fabric, a fabric is woven while yarns arranged in parallel with the yarns to be removed are folded. After weaving, a crimp of folded yarns is set by heat-treatment (first time), then the yarns to be removed are removed, and further heat-treatment (second time) is carried out in order to maximize and set the crimp of the folded yarns, and thus the woven fabric is obtained. At this time, it is preferable that the heat treatment temperature after removing the yarns to be removed be adjusted equal to or lower than the heat treatment temperature before removing the yarns to be removed. In this manner, a pleated shape superior in shape retention and followability can be arbitrarily obtained without impairing the stretchability of the woven fabric.

Hereinafter, the manufacturing method will be described in detail.

[First Step]: Weaving Step

Yarns to be used as warps and wefts are prepared, and the warps are appropriately subjected to preparation steps such as warping and starching to prepare warp beams.

Next, the warp beams and the wefts are mounted to a loom and a fabric is woven. As a loom to be employed, a water jet loom, a rapier loom, an air jet loom, or the like may be appropriately used according to the application. The weave structure is not particularly limited and may be determined appropriately.

In the weaving step, at least two types of yarns, including yarns that are to constitute a woven fabric and yarns that are to be removed in a later step and are not to exist in the final woven fabric, are used as yarns (warps or wefts) extending along the direction intersecting with the pleating direction. As warps or wefts, yarns to be removed are arranged at appropriate intervals between yarns to constitute a woven fabric. Although thermoplastic fibers are preferable as the yarns to constitute a woven fabric and inelastic fibers are more preferable as described above, thermoplastic fibers, and moreover inelastic fibers are preferable also as the yarns to be removed.

Hereinafter, the case where two types of yarns are used as yarns to intersect with the pleating direction is explained where a yarn that is to finally constitute a woven fabric is referred to as "warp (weft) A" and a yarn to be removed that is not to finally exist in the woven fabric is referred to as "warp (weft) B". On the other hand, a yarn arranged in the pleating direction is referred to as "weft (warp)" in the explanation.

The warps (wefts) A, which are yarns intersecting with the pleating direction and which are to eventually constitute a woven fabric, may be made of, for example, various synthetic fibers such as nylon fibers and polyester fibers. Above all, inelastic polyester fibers are preferable in view of strength and dimensional stability. Examples of the inelastic polyester fiber include fibers made of polyethylene terephthalate, polybutylene terephthalate, polypropylene terephthalate, a copolymer thereof, or the like.

It is preferable that part or all of the warps (wefts) A be multifilaments composed of filaments having a single yarn diameter of 6 μm or less. Such filaments are not particularly limited, and may be obtained by direct spinning or may be obtained by subjecting sea-island composite fibers to removal of the sea component. It is preferable to adjust the single yarn diameter into the above range because a pleated shape is likely to be formed more stably and regularly because the flexibility of the woven fabric is improved and the pleated shape is likely to be formed due to the resultant formation of a denser structure.

Preferably, the warps (wefts) B, which are yarns extending in a direction intersecting with the pleating direction and are not to finally exist in the woven fabric, are constituted by soluble yarns because they are to be removed in a post step. The soluble yarns are fibers that exhibit solubility in solvents such as water and alkaline solutions. Specific examples of soluble yarns that can be used include, but are not limited to, water-soluble fibers such as polyvinyl alcohol-based fibers, and alkali-soluble fibers such as polyester-based fibers copolymerized with a third component such as isophthalic acid, sodium 5-sulfoisophthalate, and methoxypolyoxyethylene glycol, and polylactic acid-based fibers. Further, as the warps (wefts) B, false yarns, which are to be removed after weaving, may also be used. The yarns to be used also for the false yarns are preferably thermoplastic fibers as described above, and more preferably inelastic fiber yarns.

The total fineness of the warps (wefts) A and B is preferably 0.05 dtex to 560 dtex, more preferably 0.05 dtex to 235 dtex or less, and even more preferably 0.05 dtex to 100 dtex or less.

When warps (wefts) extending in the pleating direction have a structure composed of two or more layers, the warps (wefts) B are preferably arranged in the middle of the structure.

During weaving, it is preferable to perform the weaving with the tension applied to the warps (wefts) B being made higher than that applied to the warps (wefts) A and with the tension applied to the warps (wefts) A being made lower than that applied to the warps (wefts) B as long as the weaving is not hindered. In such a tension relationship between the warps (wefts) A and B, the wefts (warps) extending in the pleating direction are restrained by the warps (wefts) A with the warps (wefts) B as a fulcrum, and the warps (wefts) A are to be pushed into the cloth side with the warps (wefts) A being slack, so that the slack warps (wefts) A are folded to exhibit crimp. At the time of inserting wefts (warps), arranging the wefts (warps) alternately at the upper and lower positions of the warps (wefts) B makes the warps (wefts) A that restrain the wefts (warps) arranged on the upper side (lower side) easier to be pushed to the upper side (lower side) while making the warps (wefts) A that restrain the wefts (warps) arranged on the lower side (upper side) easier to be pushed to the lower side (upper side), during the course of pushing wefts (warps) by beating, a scouring step (described below), or the like, viewing in the positional relation with the warps (wefts) B. As a result, the warps (wefts) A are alternately folded up and down to exhibit crimp. By doing so, the crimp is heat-set by a subsequent heat treatment (described later) and the warps B are removed, whereby a fine pleated shape as described above can be imparted to the woven fabric. In inserting the wefts (warps), the warps (wefts) B may be alternately arranged one by one at the upper and lower positions, or a plurality of warps (wefts) B may be alternately arranged at the upper and lower positions of the warps (wefts) B. Further, in the case of alternately arranging a plurality of yarns, the plurality of wefts (warps) may be inserted at a time, or may be divided and inserted continuously.

For example, in order to stably and regularly form a pleated shape, it is preferable that the tension of the warps (wefts) B be 0.5 to 1.5 cN/dtex and the tension of the warps (wefts) A be 0.05 to 0.15 cN/dtex. The arrangement of the warps (wefts) A and the warps (wefts) B can be appropriately adjusted according to the application, but it is preferable to arrange them with a ratio of one warp B for 2 to 10 warps A.

Like the yarns explained as the warps (wefts) A, which are yarns extending in a direction intersecting with the pleating direction and are to finally constitute a woven fabric, the yarns extending in the pleating direction can be constituted by various synthetic fibers such as nylon fibers and polyester fibers, and they are preferably inelastic yarns. Above all, inelastic polyester fibers are preferable in view of strength and dimensional stability. Examples of the inelastic polyester fiber include fibers made of polyethylene terephthalate, polybutylene terephthalate, polypropylene terephthalate, or the like.

Preferably, part or all of the yarns to be used in the pleating direction are multifilaments composed of filaments having a single yarn diameter of 6 μm or less, and may be obtained by direct spinning or may be obtained by subjecting sea-island composite fibers to removal of the sea component, without any particular limitations. It is preferable to adjust the single yarn diameter into the above range because the flexibility of the woven fabric is improved and a denser structure can be obtained.

The total fineness of the yarns to be used in the pleating direction is preferably 560 dtex or less, more preferably 235 dtex or less, and even more preferably 100 dtex or less.

In addition, by using two or more types of yarns used as the yarns to be used in the pleating direction, the physical characteristics of the pleated shape in the woven fabric can be appropriately adjusted. For example, by using rigid monofilaments as at least one type of yarns, the shape retention of the pleated shape can be further improved. Further, it is preferable that the yarns extending in the pleating direction be arranged in two or more layers to form a woven fabric.

The woven fabric of the present invention can be processed into a tubular form and be used as a substrate of artificial blood vessels or the like; when it is processed into a tubular woven fabric, the inner diameter thereof is preferably 100 mm or less, more preferably 50 mm or less, and even more preferably 10 mm or less. A preferable lower limit is about 1.5 mm from the viewpoint of weaving performance.

[Second Step]: Post-Processing Step

The post-processing step is preferably performed, for example, via the steps described below.

The woven fabric is subjected to scouring, e.g., washing with hot water, to remove oil on the yarns and starch, and to shrunk fibers when thermoplastic fibers are used for the warps (wefts) B. The processing conditions are preferably a temperature of 80 to 98° C. and a time of 15 to 40 minutes. The scouring agent is not particularly limited, and a commercially available scouring agent may be appropriately used.

Next, the crimp shape of the warps (wefts) A is stabilized by a pre-heat setting (first heat treatment). At this time, it is more preferable that the warps (wefts) B are thermoplastic fibers and have been shrunk in the previous step because the crimp of the warps (wefts) A increases with the shrink. The processing conditions of the pre-heat setting are preferably a temperature of 160 to 190° C. and a time of 3 to 10 minutes.

Next, the removal of the sea component of the woven fabric is performed as necessary, and the warps (wefts) B are removed. When the warps (wefts) B are soluble yarns, the removal of the sea component and the dissolution and removal are performed by the following steps. When the warps (wefts) B are not soluble yarns but false yarns, the false yarns are physically removed by pulling them out from the woven fabric.

(a) Acid Treatment

The sea component of the sea-island composite fibers is embrittled by acid treatment. The acid is not particularly limited and may be, for example, maleic acid. The processing conditions are preferably a concentration of 0.1 to 1% by mass, a temperature of 100 to 150° C., and a time of 10 to 50 minutes. When sea-island composite fibers are not used, the acid treatment can be omitted.

(b) Alkali Treatment

The sea component of the sea-island composite fibers that has been embrittled by the acid treatment as well as the soluble yarn are dissolved by alkali treatment. Examples of the alkali is not particularly limited and may be, for example, sodium hydroxide. The processing conditions are preferably a concentration of 0.5 to 2% by mass, a temperature of 70 to 98° C., and a time of 60 to 100 minutes.

Next, the crimp of the warps (wefts) A loosened by the sea component removal treatment is maximized again by heat setting (second heat treatment). Here, the heat treatment is performed in a state where the woven fabric is maximally compressed in a direction intersecting with the pleating direction so as not to wrinkle. The processing conditions are preferably a temperature of 160 to 190° C. and a time of 3 to 10 minutes. In addition, the heat setting (third time) may be performed again for the purpose of forming a woven fabric having a shrink margin while leaving the crimp bending point, but the third heat setting may be omitted if necessary or may be carried out twice or more. The processing conditions are preferably a temperature 10 to 20° C. lower than that of the first heat setting, and a time of 3 to 10 minutes.

In this way, it is possible to provide a highly versatile woven fabric being superior in followability and capable of being sewn while maintaining the folding structure in which a folding shape is stably formed. Further, when the woven fabric is processed into a tubular shape, it becomes a tubular woven fabric superior in stretchability, flexibility, and kink resistance (pliability). Therefore, the tubular woven fabric can be used usefully for industrial applications such as transport hoses for a fluid or a powder and protective hoses for linear bodies such as wires, cables and conduits, and tubular filters, as well as medical applications such as substrates of artificial blood vessels and stent grafts, and in particular, can be suitably used as artificial blood vessels. Further, according to the manufacturing method of the present invention, the above-described woven fabric can be manufactured well.

The FIGURE schematically shows one embodiment of the woven fabric obtained as described above. In this drawing, in order to clearly show the insertion position of the wefts (warps) extending in the pleating direction, the pleat mountain parts $6\text{-}A_i$, $6\text{-}A_{ii}$ of two adjacent warps (wefts) $A_i$, $A_{ii}$ arranged in a direction intersecting with the pleating direction are drawn far apart from each other, and the ridges formed between the pleat mountain parts are also drawn large. However, actually, the pleat mountain parts $6\text{-}A_i$, $6\text{-}A_{ii}$ are very close in the horizontal direction in the drawing, and the ridges formed therebetween are extremely small, and therefore the pleat mountain parts $6\text{-}A_i$, $6\text{-}A_{ii}$ can be considered to form substantially one pleat. The same applies to the pleated valley parts $7\text{-}A_i$, $7\text{-}A_{ii}$.

EXAMPLES

Hereafter, examples of the present invention will be described together with comparative examples.

Methods for measuring the characteristics used in the examples are as follows.

(1) Fineness, Number of Filaments

The fineness was measured according to fineness based on corrected mass (Method A) as specified in JIS L 1013:2010 8.3.1. The number of filaments was measured according to JIS L 1013:2010 8.4.

(2) Average Diameter of Yarns Arranged in the Same Direction as Pleats

A woven fabric was cut in a direction intersecting with the pleating direction, and the cross section of a yarn bundle arranged in the pleating direction was enlarged 400 magnifications and photographed with a microscope VHX-2000 manufactured by KEYENCE CORPORATION. On the basis of the photograph, the distance between the vertices of the top and the bottom of the yarn bundle in the vertical direction (the thickness direction) was measured in μm unit, and the average value thereof was calculated. At that time, the measurement was performed five times while changing samples, and the average was evaluated.

(3) Single Yarn Diameter

The single yarn diameter was measured on the basis of a cross sectional photograph of the multifilament to be used taken at 400 magnifications with a microscope VHX-2000 manufactured by KEYENCE CORPORATION, and was calculated in μm unit. At this time, a modified cross-section yarn, such as a flat yarn, was measured at a site where a minimum value was afforded. The measurement was performed five times while changing samples, and the average was evaluated.

(4) Pleat Height

A woven fabric after post-processing was cut in a direction perpendicular to the pleating direction, and the cut surface was enlarged 400 magnifications and photographed with a microscope VHX-2000 manufactured by KEYENCE CORPORATION. On the basis of the photograph, the mountain top part and the valley bottom part of the pleats of one warp (weft) extending in a direction intersecting with the pleating direction at the front of the photograph (i.e., the warp (weft) A, indicated by symbol 1 in the FIGURE) are vertically connected by a line, and the length thereof was measured and the pleat height was calculated in μm unit. At that time, the measurement was performed five times while changing samples, and the average was evaluated.

(5) Weave Density

Weave density was measured according to JIS L 1096: 2010 8.6.1 (Method A).

A sample was placed on a flat table, and unnatural wrinkles and tension were removed. Then, the number of warps and wefts existing within a distance of 0.5 cm were counted at 5 different sites and their average was calculated and converted into the number per 2.54 cm.

(6) Sewability

Whether a pleated shape is maintained or not by machine sewing was evaluated. The pleated shape after sewing was visually observed and evaluated in three stages of ⊚, ○, and x.

⊚: A pleated shape is maintained.

○: A pleated shape is crushed, but mountain parts and valley parts can be confirmed.

x: The pleats were completely crushed and the shape was not maintained.

(7) Bending Resistance

A sample was cut into 10 cm×10 cm, placed on a flat table, and folded in half in a direction intersecting with the pleating direction. A load of 100 g was applied to the entire surface for 10 seconds, and then the state of the fold was visually observed and evaluated by ⊚, Δ, and x.

⊚: No crease can be confirmed.

○: Creases can be confirmed, but they will turn into an original state when they are extended by hand.

x: Creases can be clearly confirmed, and they will not turn into an original state even if they are extended by hand.

Example 1

As a weaving step, the following yarns A, B, and C were arranged such that warps were yarns intersecting with the pleating direction, and there was woven a weft-double woven fabric in which the weave density after post-processing was as follows: the warps A: 200 yarns/inch (2.54 cm) and the wefts C: 306 yarns/inch (2.54 cm).

Warp A (sea-island composite fibers): polyethylene terephthalate fiber, 66 dtex, 9 filaments (after removal of the sea component: 53 dtex, 630 filaments)

Warp B (soluble yarn): easily alkali-soluble polyester fiber copolymerized with sodium 5-sulfoisophthalate, 84 dtex, 24 filaments Weft C (sea-island composite fiber): polyethylene terephthalate fiber, 66 dtex, 9 filaments (after removal of the sea component: 53 dtex, 630 filaments)

The warps A and the warps B were arranged such that these were repeated at a ratio of one warp B to three warps A. A warp B was arranged such that it passed between two wefts C having a double-layer structure.

Next, as a post-processing step, the resulting weft-double woven fabric was washed with hot water at a temperature of 98° C. for a time of 20 minutes, and then subjected to pre-heat setting at a temperature of 180° C. for a time of 5 minutes. Next, the resulting weft-double woven fabric was subjected to the removal of the sea component of the warps A and the wefts C and to the dissolution and removal of the warps B. The acid treatment was performed using maleic acid under the treatment conditions specified by a concentration of 0.2% by mass, a temperature of 130° C. and a time of 30 minutes, and the alkali treatment was performed using sodium hydroxide under the treatment conditions specified by a concentration of 1% by mass, a temperature of 80° C. and a time of 90 minutes. Finally, heat setting was performed at a temperature of 180° C. for a time of 5 minutes.

The properties of the obtained woven fabric are shown in Table 1. Among the constituent yarns of the obtained woven fabric, the ratio of the thermoplastic fibers was 100% by mass, and the average diameter of the yarns arranged in the same direction as the pleats was 70 μm. The pleat height was 270 μm. Both the bending resistance and the sewability of the obtained woven fabric were ⊚.

Example 2

A woven fabric was obtained in the same manner as in Example 1, except that a weft-double woven fabric in which the weave density of the wefts C after post-processing was 96 yarns/inch (2.54 cm) was worn such that the pleat height after the post-processing was 650 μm, and that black solution-dyed yarns (polyethylene terephthalate fibers, 56 dtex, 18 filaments) were used as warps B and the warp B was pulled out after removal of the sea component. The properties of the obtained woven fabric are shown in Table 1. Among the constituent yarns of the obtained woven fabric, the ratio of the thermoplastic fibers was 100% by mass, and the average diameter of the yarns arranged in the same direction as the pleats was 70 μm. The obtained woven fabric had a bending resistance of ⊚ and a sewability of ○.

Example 3

A woven fabric was obtained in the same manner as in Example 1, except that the following yarns were used as warps A and wefts C, which were arranged at a ratio of three warps A1 to two warps A2, and heat setting (third time) after post-processing was performed at a temperature of 160° C. for a time of 5 minutes such that the pleat height after the post-processing was 150 μm.

Warp A1: Polyethylene terephthalate fiber, 48 dtex, 144 filaments

Warp A2: Cotton yarn, 80 counts (about 74 dtex) Weft C: Polyethylene terephthalate fiber, 48 dtex, 144 filaments The properties of the obtained woven fabric are shown in Table 1. Among the constituent yarns of the obtained woven fabric, the ratio of the thermoplastic fibers was 68% by mass, and the average diameter of the yarns arranged in the same direction as the pleats was 67 μm. The bending resistance of the obtained woven fabric was ○ and the sewability was ⊚.

Example 4

A woven fabric was obtained in the same manner as in Example 3, except that the warps A were arranged at a ratio of two warps A1 to three warps A2. The properties of the obtained woven fabric are shown in Table 1. Among the constituent yarns of the obtained woven fabric, the ratio of the thermoplastic fibers of the yarns intersecting with the pleating direction was 52% by mass, and the average diameter of the yarns arranged in the same direction as the pleats was 67 μm. Regarding the bending resistance of the obtained woven fabric, wrinkles caused by the deterioration of followability were deeper than those in Example 3, but were in the category of ○, which was a practically acceptable degree. The sewability was ⊚.

Comparative Example 1

A woven fabric was obtained in the same manner as in Example 1, except that the third heat setting was performed at a temperature of 160° C. for a time of 5 minutes such that the pleat height after the post-processing was 110 μm. The properties of the obtained woven fabric are shown in Table 1. Among the constituent yarns of the obtained woven fabric, the ratio of the thermoplastic fibers was 100% by mass, and the average diameter of the yarns arranged in the same direction as the pleats was 70 μm. The bending resistance of the obtained woven fabric was x, and the sewability was ⊚.

Comparative Example 2

A woven fabric was obtained in the same manner as in Example 1, except that a weft-double woven fabric in which the weave density of the wefts C after post-processing was 45 yarns/inch (2.54 cm) was worn such that the pleat height after the post-processing was 800 μm. The properties of the obtained woven fabric are shown in Table 1. Among the constituent yarns of the obtained woven fabric, the ratio of the thermoplastic fibers was 100% by mass, and the average diameter of the yarns arranged in the same direction as the pleats was 70 μm. The bending resistance of the obtained woven fabric was ⊚, and the sewability was x.

DESCRIPTION OF REFERENCE SIGNS

1: Warp (weft) $A_i$ extending in the direction intersecting with the pleating direction
2: Warp (weft) $A_{ii}$ extending in the direction intersecting with the pleating direction
3: Weft (warp) extending in the pleating direction
4: Weft (warp) extending in the pleating direction
5: Pleat height
6: Mountain part of pleat
6-$A_i$, 6-$A_{ii}$: Mountain part of a pleat of two adjacent warps (wefts) $A_i$, $A_{ii}$
7: Valley part of pleat
7-$A_i$, 7-$A_i$: Valley part of a pleat of two adjacent warps (wefts) $A_i$, $A_{ii}$

The invention claimed is:

1. A woven fabric having a pleat, wherein
the woven fabric is a weft-double woven fabric or warp-double woven fabric in which warps or wefts are arranged such that they pass between two wefts or warps having a double-layer structure in a pleated state, and the woven fabric has a single-layer structure in an un-pleated state when sides of the woven fabric are pulled,
the pleat is in a state in which a mountain part and a valley part are formed alternately and repeatedly on both the front and back sides of a textile and the mountain parts of the front side of the textile are the valley parts on the back side of the textile, and
the pleat has a height of 2 to 10 times an average diameter of a yarn arranged in the same direction as the pleat.

TABLE 1

| | Yarn intersecting with pleats | | | | | | |
|---|---|---|---|---|---|---|---|
| | Fiber A1 | | | Fiber A2 | | | |
| | Yarn type | Single yarn diameter (μm) | Total fineness (dtex) | Yarn type | Single yarn diameter (μm) | Total fineness (dex) | Method of fiber B removal | Ratio of thermoplastic fiber (%) |
| Example 1 | PET | 2.8 | 53 | — | — | — | Dissolution | 100 |
| Example 2 | PET | 2.8 | 53 | — | — | — | Pulling out | 100 |
| Example 3 | PET | 5.6 | 48 | cotton | — | 74 (80 counts) | Dissolution | 68 |
| Example 4 | PET | 5.6 | 48 | cotton | — | 74 (80 counts) | Dissolution | 52 |
| Compartive Example 1 | PET | 2.8 | 53 | — | — | — | Dissolution | 100 |
| Compartive Example 2 | PET | 2.8 | 53 | — | — | — | Dissolution | 100 |

| | Yarn in pleating direction | | | | | | |
|---|---|---|---|---|---|---|---|
| | Fiber C1 | | | | | | |
| | Yarn type | Single yarn diameter (μm) | Yarn diameter (μm) | Total fineness (dtex) | Average diameter (μm) | Pleat height (μm) | Bending resistance | Sewability |
| Example 1 | PET | 2.8 | 70 | 53 | 70 | 270 | ⊙ | ⊙ |
| Example 2 | PET | 2.8 | 70 | 53 | 70 | 650 | ⊙ | ○ |
| Example 3 | PET | 5.6 | 67 | 48 | 67 | 150 | ○ | ⊙ |
| Example 4 | PET | 5.6 | 67 | 48 | 67 | 150 | ○ | ⊙ |
| Compartive Example 1 | PET | 2.8 | 70 | 53 | 70 | 110 | X | ⊙ |
| Compartive Example 2 | PET | 2.8 | 70 | 53 | 70 | 800 | ⊙ | X |

INDUSTRIAL APPLICABILITY

The pleated woven fabric according to the present invention can be suitably used for medical material applications such as general clothing and artificial blood vessels, and other industrial material applications, but the application range is not limited thereto.

2. The woven fabric according to claim 1, wherein 60% by mass or more of the yarn constituting the woven fabric is a thermoplastic fiber.

3. The woven fabric according to claim 2, wherein the thermoplastic fiber is an inelastic fiber.

4. The woven fabric according to claim 3, wherein the inelastic fiber a polyester fiber.

5. The woven fabric according to claim 1, wherein part or all of the yarns constituting the woven fabric are multifilaments composed of filaments having a single yarn diameter of 6 μm or less.

6. The woven fabric according to claim 1, wherein the woven fabric is used for medical use.

7. The woven fabric according to claim 1, wherein the woven fabric is in a tubular form.

8. An artificial blood vessel comprising the woven fabric in a tubular form according to claim 7 as a substrate.

9. A method for manufacturing the woven fabric according to claim 1, comprising steps (a) to (d):
- (a) a step of using a yarn to be removed as part of warps or wefts and weaving a fabric while folding a yarn arranged in parallel with the yarn to be removed,
- (b) a heat treatment step of setting a crimp of the folded yarn,
- (c) a step of removing the yarn to be removed after the step (b),
- (d) a heat treatment step of setting the crimp of the folded yarn after the step (c).

* * * * *